(12) United States Patent
Rosenthal et al.

(10) Patent No.: US 6,254,625 B1
(45) Date of Patent: Jul. 3, 2001

(54) HAND SANITIZER

(76) Inventors: Cenayda V. Rosenthal; Richard A. Rosenthal, both of 2680 Pacer La., San Jose, CA (US) 95111

( * ) Notice: Subject to any disclaimer, the term of this patent is extended or adjusted under 35 U.S.C. 154(b) by 0 days.

(21) Appl. No.: 09/109,452

(22) Filed: Jul. 2, 1998

(51) Int. Cl.$^7$ .................................................. A61N 7/00

(52) U.S. Cl. ............................. 607/88; 607/90; 607/94; 606/2; 606/10; 606/11; 606/13

(58) Field of Search .................... 607/88–95; 606/2–13; 422/28

(56) References Cited

U.S. PATENT DOCUMENTS

| | | | | |
|---|---|---|---|---|
| 4,078,747 | * | 3/1978 | Minovitch | 244/159 |
| 5,536,400 | * | 7/1996 | Schultz | 210/192 |
| 5,614,151 | * | 3/1997 | LeVay et al. | 422/24 |
| 6,010,727 | * | 1/2000 | Rosenthal | 426/240 |

\* cited by examiner

*Primary Examiner*—Linda C. M. Dvorak
*Assistant Examiner*—R. Kearney
(74) *Attorney, Agent, or Firm*—Walter A. Hackler

(57) ABSTRACT

A hand sanitizer generally includes an ozone producing, germicidal ultraviolet lamp for oxidizing organic debris and inactivating bacteria and viruses on the surface and subsurface of hands. In addition, a polychromatic light source is provided for destruction of residual ozone and photoreactivating, or photorepairing, ultraviolet induced effects on the skin. The lamps may be disposed in a free standing housing having a chamber for containing the produced ozone and receiving hands in a vertical orientation. Fans may be provided for circulating the ozone and atmospheric gas throughout the chamber and for evaporating residual moisture from the skin. A light source for destroying excess ozone is also provided which may be operated after the organic debris has been oxidized. Shields are provided within the chamber in order to protect a user's eyes from exposure to the ultraviolet light. The apparatus may be powered entirely by conventional solar panels.

12 Claims, 1 Drawing Sheet

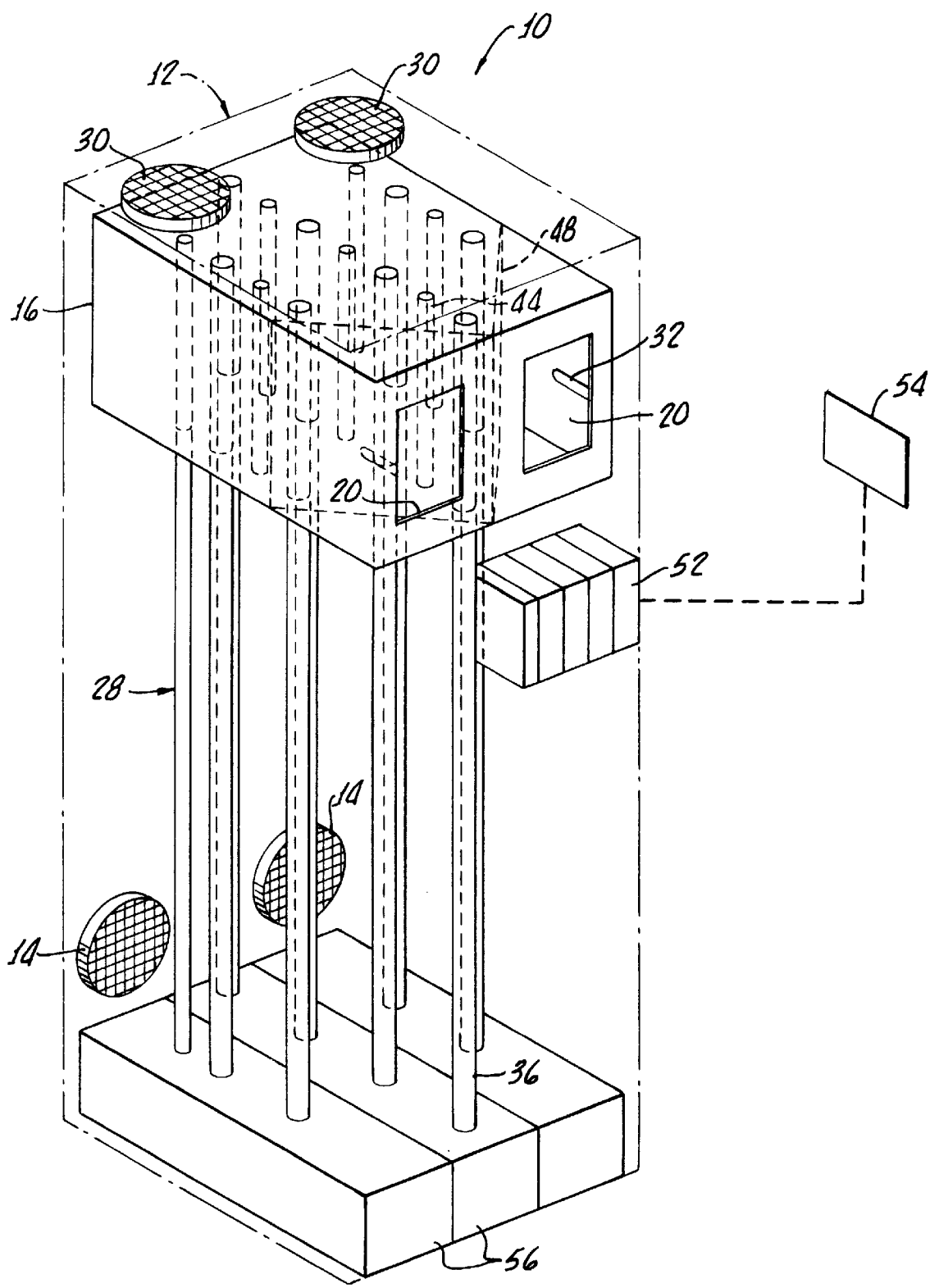

HAND SANITIZER

The present invention generally relates to apparatus and method for sanitizing skin and more specifically relates to a waterless, chemical free apparatus and method, using ozone, ultraviolet, visible and near infrared light, for inactivating pathogens commonly found on human hands.

It is now known that many forms of infectious disease, such as the common cold, are contracted and spread to others, primarily by the hands. Conventional medical wisdom teaches that the best way to prevent contraction and transmission of most common bacterial and viral infections is by thoroughly and often cleansing the hands throughout the day, and primarily before touching one's face or preparing food.

Cleansing and sanitizing an individual's hands using warm soapy water is generally effective for removing "germs" that have accumulated on hands throughout the day. For additional protection, an antibacterial hand soap may be utilized in lieu of conventional soap. Washing and rinsing of the hands is sometimes followed by applying a topical sterilant such as for example, a denatured alcohol, an anti-bacterial hand gel or anti-bacterial hand lotion to further protect the hands. Although these measures will help to control the spread of many pathogens residing on the skin, they are ineffective if not performed routinely and methodically. Unfortunately, routine use of antibacterial soaps, lotions and gels may cause chapping of the skin or other undesirable reactions, especially for those persons being sensitive to the active ingredients found in these products.

In a public restroom, although soap and/or sterilant dispensers are provided, it is often the case that the supply is depleted. This is usually only discovered after the individual has attempted to activate the dispenser by manual means, said manual means being likely contaminated by prior users.

Without an antibacterial soap, mere rinsing of the hands with warm water is not effective for eliminating bacteria on the skin. The hot water supply in an average washroom is usually much cooler than the temperature necessary to kill the vast majority of pathogens, said temperature being typically at least 150 degrees Fahrenheit or higher. In addition, portable toilet facilities typically do not have a supply of soap or water available for washing hands.

Though not widely available, germicidal lamps have been developed. These lamps utilize light at germicidal wavelengths, such as light in the UVC waveband, for destroying pathogens residing on the skin. In rare instances where a germicidal lamp is available, effectiveness may be compromised by contagium embedded underneath the fingernails or in debris which UVC radiation will not penetrate.

In the food service industry sanitation of hands is especially important for the protection of the public. Food service workers are therefore mandated by law to wash the hands after use of a restroom in order to prevent transmission of infectious disease, such as hepatitis, to food service customers. Because restrooms and wash facilities are generally private, regulations requiring hand washing of food service workers are nearly unenforceable and compliance therewith is usually only on an honor basis. However, concerns for public safety have become so great, possibly in light of more resistant strains of bacterial and viruses that have emerged in recent years, that additional safety measures have been proposed and implemented including surveillance cameras in washrooms.

The present invention provides a safe and highly effective means of sanitizing hands without the use of water, soap, gels or lotions, which is effective in destroying microorganisms on both the surface and subsurface of hands as well as beneath fingernails.

SUMMARY OF THE INVENTION

Accordingly, the present invention provides hand sanitizing apparatus which utilizes ultraviolet light to both inactivate pathogens on the hands as well as oxidize organic matter which may contain pathogens, on the surface and subsurface of the hands and embedded under fingernails, by using ozone produced by short wavelength ultraviolet light.

More particularly, the present invention may comprise, for example, a free standing unit which provides housing means for containing a series of lamps. The housing means includes means for enabling hands to be inserted into the unit while the lamps are sequentially operated as will be discussed in detail hereinafter.

First, an ultraviolet light having wavelengths less than about 184 nm is used to ionize atmospheric gas in the unit. The ozone is circulated through the unit and about the hands, oxidizing detritus or debris that may be embedded on the hands and beneath surfaces of nails. UVC light having germicidal wavelengths, for example, a peak wavelength of about 254 nm, is used for inactivation of pathogenic organisms resident on the skin surface.

Means are preferably provided for removing excess ozone after the sanitation treatment, said excess ozone being any ozone remaining in the unit after the oxidation of detritus or debris has taken place. For example, a light source having wavelengths of about 300 nm may be provided for this purpose by converting the excess ozone back into molecular oxygen.

Additionally, the present invention may include photoreactivation means, including preferably a high efficacy quartz halogen lamp, for protecting the hands from any undesirable effects of the UV light on the user's skin, by radiation of polychromatic light (Block A having wavelengths in the UVA, Soret, visible and near infrared wavelengths) [Photoreactivation]

In a broader aspect of the present invention, skin sanitizing apparatus may be provided which is used to treat skin other than on the hands. This can be accomplished through appropriate modifications to the apparatus housing.

Importantly, due to its minimal energy requirements, the apparatus of the present invention may be used in conjunction with solar panels to provide a means for sterilizing hands, while outdoors such as in the field where effective sterilization of would be otherwise unavailable. Accordingly, an even broader aspect of the present invention includes apparatus for sanitizing surfaces, for example, surfaces of food products, using a series of solar powered lamps designed to produce ozone, eliminate excess ozone and destroy pathogens on the surface with germicidal light.

The apparatus described briefly hereinabove and in greater detail hereinafter, is suitable for performing a method for sanitizing skin in accordance with the present invention. The method may include preprogrammed, sequential, and preferably timed, operation of the lamps for ensuring maximum effectiveness.

For example, a method in accordance with the invention may comprise initiating an ozone producing lamp and causing hands to be immersed in the produced ozone for a period of about six seconds during which the ozone oxidizes organic matter and debris on the surface and subsurface of the hands. During this period, germicidal ultraviolet light is radiated onto the hands for inactivation of pathogens on the hand surfaces. A Block A light source is then used to convert excess ozone back to molecular oxygen. In addition, the method may include radiating a polychromatic light at the hands for causing photoreactivation thereof.

BRIEF DESCRIPTION OF THE DRAWING

The present invention will be more clearly understood when considering the accompanying drawing of which:

FIG. 1 shows a schematic view of a hand sanitizer in accordance with the present invention which is suitable for performing a method for sanitizing hands in accordance with the invention.

DETAILED DESCRIPTION

Turning now to FIG. 1, a hand sanitizer 10 in accordance with the present invention is shown in schematic format to more clearly illustrate the components thereof. While any suitable size may be utilized, the hand sanitizer may have an overall size of 5'×2'×1.5', for example. The sanitizer 10 may generally include a free standing housing 12, having intake fans 14 for drawing atmospheric gas, i.e. air, into a sanitizing chamber 16 within the housing 12. Slots 20 in communication with the chamber 16 provide means for enabling insertion of hands (not shown) of a user (not shown), said hands being preferably inserted in a vertical orientation.

It is contemplated that the present invention is not limited to apparatus and method for sanitation of hands only, but in a broader sense may encompass apparatus and method for sanitizing skin. However, for the sake of simplicity, the following, description will be directed at apparatus and method for sanitizing hands.

Means, such as lamps 28, are provided for producing ozone from the atmospheric gas drawn into the chamber 16. More particularly, the lamps 28 may be 36 Watt ultraviolet lamps 28 providing a source of UVC light that, upon contacting the atmospheric gas, provide means for ionizing the gas. For this purpose the UVC light may have a wavelength of less than about 184 nm. Suitable lamps are available from General Electric.

The chamber 16 is infused with the produced ozone by means of one or more exhaust fans 30 in conjunction with the intake fans 14 which cause circulation of ozone and atmospheric gas through the chamber 16. Importantly, the ozone infused chamber 16 provides means for oxidizing organic matter on a surface and a subsurface of the hands, when the hands are inserted through the slots 20, in order to eliminate pathogens, for example E. coli, on the hands. The organic matter may be dirt, grease, excrement, detritus or other debris containing bacteria or viruses imbedded therein. Advantageously, the ozone will oxidize debris embedded beneath fingernails, which is difficult to remove using conventional hand washing methods.

It is noted that the present invention is effective in destroying bacteria such as E. coli, as well as viruses such as hepatitis A, in addition to most other common infectious diseases found on human skin.

A proximity sensor 32, for example an infrared sensor, may be provided for detecting the insertion of a person's hands in order to initiate the ozone producing means 28.

In addition, the present invention may comprise a source 36 of actinic radiation as means for inactivating pathogens resident on the surface of the hands while they are inserted in the chamber. The source 36 of actinic radiation may include a source of UVC light having a peak wavelength of about 254 nm. The hands may remain in the ozone infused chamber 16 for a period of about six seconds which is typically adequate for oxidizing the detritus or other debris and inactivating most bacterial pathogens. Suitable UVC light may be provided by 200 watt lamps available from Heraeus.

A polychromatic source 44 of UVB light having a wavelength of about 300 nm, may provide means for converting excess ozone into molecular oxygen which is exhausted from the chamber 16 by means of the fans 30, said excess ozone being any of the produced ozone that has not been utilized for oxidation of the organic matter. The polychromatic light source 44 may be initiated after the oxidation and inactivation period has expired. Suitable polychromatic UVC light is produced by 500 watt lamps available from General Electric.

It is believed that the exposure of skin to the ultraviolet light sources of the present invention will damage skin cells; therefore, photoreactivation means 44 is provided in order to protect hands from UV damage. "Photoreactivation" is a term in the art used to describe the repair of living cells by the use of light.

Preferably, a polychromatic light, having wavelengths of between about 300 nm in the UVB and about 380 nm in the UVA waveband, about 450 nm in the Soret waveband, about 550 nm in the visible waveband and between about 660 nm and about 720 nm in the near infrared waveband, is provided for photoreactivation. The source of such light is preferably provided by suitable means such as a filtered infrared lamp. More preferably, however, the source of such light is a 500 watt, high efficacy quartz halogen lamp 44, available from General Electric. This is a high intensity gas discharge lamp.

Accordingly, after the oxidation and inactivation period, the ultraviolet lamps 28 and 36 are turned off, and the hands may remain in the chamber for an additional three seconds for destruction of excess ozone by means of the UVB lamps 44, and photorepair of the skin by the quartz halogen lamps 44. Any residual moisture on the hands is evaporated by the quartz halogen lamps 44 and the atmospheric gas cycling through the chamber 16.

Importantly, a shield 48 for each ultraviolet light source 28, 36 is provided for protecting eyes of the user or any passerbyers from exposure to the ultraviolet light 28. Proper angling of the shields 48 will ensure that they will be effective even when persons may be directly looking at the apparatus 10 while it is in operation. For example, each shield 48 may be disposed at an angle of about 45 degrees between each ultraviolet lamp 28 and the insertion slots 20.

In addition still, a programmable logic controller 52 is preferably provided as timing means for initiating and sequentially operating the fans 14, 30, ultraviolet lamps 28 and 36 and the high efficacy quartz halogen lamps 44. The apparatus 10 may be powered by any suitable means, however, due to its minimal energy requirements, (i.e. a total of about 2700 watts) the hand sanitizer 10 may be solar powered by conventional panels 54.

Conventional electronic ballasts 56 may provide means for regulating the lamps 28, 36.

It should now be appreciated that a method for sanitizing hands in accordance with the present invention may be comprised of the steps of producing ozone by radiating UVC light into atmospheric gas having wavelengths of less than about 184 nm in order to ionize the atmospheric gas and oxidizing organic matter on surface and subsurface of hands, with the produced ozone by causing the hands to be immersed in the produced ozone for a period of about six seconds.

Additional steps may include inactivating pathogens on the immersed hands by radiating, at the ozone immersed hands, UVC light having a peak wavelength at about 254 nm during the period of about six seconds and subsequently photoreactivating the UVC irradiated hands by radiating a polychromatic light having wavelengths of between about 300 nm in UVB and about 380 nm in the UVA waveband, about 450 nm in the Soret waveband, about 550 nm in the visible waveband and between about 660 nm and about 720 nm in the near infrared waveband, at the UVC irradiated hands for a period of about three seconds following the period of about six seconds.

A further step may include converting excess ozone to molecular oxygen by radiating UVB light having a wavelength of about 300 nm at the hands during the period of about three seconds, said excess ozone being any of the produced ozone that has not been utilized for oxidation of the organic matter. In addition still, the method may comprise shielding the eyes of a user from exposure to the UVA, UVB and UVC radiation and evaporating residual moisture from the irradiated hands by initiating exhaust fans to circulate atmospheric gas about the hands during the photoreactivating step.

The effectiveness of the present invention in eliminating pathogens, such as bacteria embedded beneath the fingernails, that are difficult to eliminate by traditional hand sterilization methods, makes the present invention particularly applicable to the food service industry and other such industries where cleanliness is especially important.

However, it is contemplated that the present invention is useful in many other environments, for example in a public restroom in addition, or alternative to, conventional washing facilities. Because the present invention requires no water or plumbing hookups, and the fact that it may be solar powered due to its minimal energy requirements, the apparatus 10 is especially useful in situations where plumbing is unavailable, such as at portable toilet facilities.

In this respect, it will be appreciated that a broader application of the present invention includes apparatus for sanitizing a surface of an article, for example, an item of food, using a series of solar powered lamps designed to produce ozone for oxidizing debris, eliminate excess ozone and destroy pathogens on the surface with germicidal light in accordance with the principles described hereinabove. Because the apparatus may be powered entirely by conventional solar panels, it may be placed in the backcountry region of a federal or state park for use as a hand, food, drink or medical equipment sterilizer for campers, rescue workers or those in charge of overseeing the backcountry.

Although there has been hereinabove described a hand sanitizer and method for sanitizing hands, in accordance with the present invention, for purposes of illustrating the manner in which the invention may be used to advantage, it will be appreciated that the invention is not limited thereto. Accordingly, any and all modifications, variations, or equivalent arrangements which may occur to those skilled in the art should be considered to be within the scope of the present invention as defined in the appended claims.

What is claimed is:

1. Skin sanitizing apparatus comprising:
   means for radiating skin with actinic radiation in order to inactivate pathogens thereon; and
   photoreactivation means, including a source of polychromatic light, for repairing actinic radiation damage to the skin.

2. The skin sanitizing apparatus according to claim 1 wherein the polychromatic light has wavelengths of between about 300 nm in UVB and about 380 nm in the UVA waveband, about 450 nm in the Soret waveband, about 550 nm in the visible waveband and between about 660 nm and about 720 nm in the near infrared waveband.

3. Skin sanitizing apparatus comprising:
   means for radiating UVC light into atmospheric gas in order to produce ozone therefrom;
   means for enabling skin to be contacted by the ozone in order to oxidize organic matter on a surface and subsurface of the skin;
   means for radiating UVC light at germicidal wavelengths at the skin to inactivate pathogens residing thereon;
   photoreactivation means, including a source of polychromatic light, for protecting the skin from UV damage; and
   means, including a source of UVB light, for converting excess ozone to molecular oxygen, said excess ozone being any of the produced ozone that has not been utilized for oxidation of the organic matter.

4. The skin sanitizing apparatus according to claim 3 wherein the polychromatic light has wavelengths of between about 300 nm in UVB and about 380 nm in the UVA waveband, about 450 nm in the Soret waveband, about 550 nm in the visible waveband and between about 660 nm and about 720 nm in the near infrared waveband.

5. The skin sanitizing apparatus according to claim 3 wherein the means for radiating UVC light to produce ozone comprises a 36 watt ultraviolet lamp, the means for radiating UVC light at germicidal wavelengths comprises a 200 watt ultraviolet lamp, and the source of UVB light comprises a 500 watt polychromatic light which comprises a 500 watt quartz halogen lamp.

6. The skin sanitizing apparatus according to claim 5 further comprising solar panel means for powering each of the lamps.

7. Method for sanitizing hands, said method comprising the steps of:
   radiating UVC light into atmospheric gas in order to produce ozone therefrom; and immersing hands in the produced ozone in order to oxidize organic matter on a surface and subsurface of the hands.

8. The method according to claim 7 further comprising the step of radiating germicidal light at the hands in order to inactivate pathogens residing thereon.

9. The method according to claim 8 further comprising the step of radiating polychromatic light at the UVC and germicidal light radiated hands in order to protect the hands from radiation damage.

10. The method according to claim 7 further including the step of converting excess ozone into molecular oxygen, said excess ozone being any of the produced ozone that has not been utilized for oxidation of the organic matter.

11. Hand sanitizing apparatus comprising:
   means, including a source of UVC light having a wavelength of less than about 184 nm, for ionizing atmospheric gas in order to produce ozone;
   means for oxidizing organic matter on surface and subsurface of hands, with the produced ozone, in order to eliminate pathogens on the hands, said means for oxidizing including chamber means for immersing the hands in the produced ozone and means for circulating produced ozone within the chamber means and around the hands;
   means, including a source of UVC light having a peak wavelength of about 254 nm, for inactivating pathogens on the hands;

means, including a source of UVB light having a wavelength of about 300 nm, for converting excess ozone to molecular oxygen, said excess ozone being any of the produced ozone that has not been utilized for oxidation of the organic matter;

photoreactivation means, including a source of polychromatic light having wavelengths of between about 300 nm in UVB and about 380 nm in the UVA waveband, about 450 nm in the Soret waveband, about 550 nm in the visible waveband and between about 660 nm and about 720 nm in the near infrared waveband, for protecting the hands from UV induced skin damage;

shield means for protecting eyes of a user of the apparatus from exposure to the UVA, UVB and UVC lights; and timing means for initiating and sequentially operating the means for producing ozone, the means for inactivating, the means for converting, and the photoreactivation means.

12. A method for sanitizing hands, said method comprising the steps of:

producing ozone by radiating UVC light into atmospheric gas having wavelengths of less than about 184 nm in order to ionize the atmospheric gas;

oxidizing organic matter on surface and subsurface of hands, with the produced ozone by causing the hands to be immersed in the produced ozone for a period of about six seconds;

inactivating pathogens on the immersed hands by radiating, at the ozone immersed hands, UVC light having a peak wavelength at about 254 nm during the period of about six seconds;

photoreactivating the UVC irradiated hands by radiating a polychromatic light having wavelengths of between about 300 nm in UVB and about 380 nm in the UVA waveband, about 450 nm in the Soret waveband, about 550 nm in the visible waveband and between about 660 nm and about 720 nm in the near infrared waveband, at the UVC irradiated hands for a period of about three seconds following the period of about six seconds;

converting excess ozone to molecular oxygen by radiating UVB light having a wavelength of about 300 nm at the hands during the period of about three seconds, said excess ozone being any of the produced ozone that has not been utilized for oxidation of the organic matter;

shielding the eyes of a user from exposure to the UVA, UVB and UVC radiation; and evaporating residual moisture from the irradiated hands by initiating exhaust fans to circulate atmospheric gas about the hands during the photoreactivating step.

\* \* \* \* \*